United States Patent [19]

Thomas et al.

[11] Patent Number: 4,517,011

[45] Date of Patent: May 14, 1985

[54] N-SUBSTITUTED HALOGENOACETANILIDES AND THEIR USE AS HERBICIDES

[75] Inventors: Rudolf Thomas; Wilfried Draber, both of Wuppertal; Robert R. Schmidt, Cologne; Ludwig Eue, Leverkusen, all of Fed. Rep. of Germany

[73] Assignee: Bayer Aktiengesellschaft, Leverkusen, Fed. Rep. of Germany

[21] Appl. No.: 869,068

[22] Filed: Jan. 12, 1978

[30] Foreign Application Priority Data

Feb. 2, 1977 [DE] Fed. Rep. of Germany ....... 2704281
Sep. 22, 1977 [DE] Fed. Rep. of Germany ....... 2742583

[51] Int. Cl.$^3$ .................... A01N 43/50; A01N 43/64; C07D 231/12; C07D 233/61
[52] U.S. Cl. .................................... 71/92; 71/95; 548/253; 548/255; 548/262; 548/337; 548/341; 548/375; 548/376; 548/377; 548/378; 548/561
[58] Field of Search ............ 548/375, 376, 377, 378, 548/341, 337; 71/92, 95; 260/308 R, 308 A, 308 D, 326.43

[56] References Cited

U.S. PATENT DOCUMENTS

| | | |
|---|---|---|
| 3,547,620 | 12/1970 | Olin ................................. 71/93 |
| 3,819,661 | 6/1974 | Maravetz ..................... 260/347.2 |
| 3,832,383 | 8/1974 | Olin ................................. 71/90 |
| 3,901,917 | 8/1975 | Richter et al. ................... 71/90 |
| 3,907,544 | 9/1975 | Olin ................................. 71/92 |
| 4,055,410 | 10/1977 | Cheng ............................. 71/92 |

FOREIGN PATENT DOCUMENTS 2405510 8/1974 Fed. Rep. of Germany .......... 71/90

*Primary Examiner*—Richard Raymond
*Attorney, Agent, or Firm*—Felfe & Lynch

[57] ABSTRACT

The invention relates to new N-substituted halogenoacetanilides of the general formula

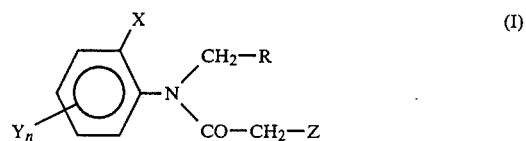

in which R represents an optionally substituted N-containing heterocyclic radical, X and Y which may be identical or different, each represent alkyl, Z represents halogen and n represents 0, 1 or 2, and their acid addition salts and metal salt complexes, to a process for the preparation of the new compounds and to their use as herbicides.

17 Claims, No Drawings

N-SUBSTITUTED HALOGENOACETANILIDES AND THEIR USE AS HERBICIDES

BACKGROUND OF THE INVENTION

1. Field of the Invention

The present invention relates to certain new N-substituted halogenoacetanilides, to a process for their preparation and to their use as herbicides, especially as selective herbicides.

2. Discussion of the Prior Art

It has already been disclosed in U.S. Pat. No. 3,442,945 and German Offenlegungsschrift No. 2,328,340 that certain chloroacetanilides, such as, for example, 2,6-diethyl-N-methoxy-methyl-chloroacetanilide and 2-ethyl-6-methyl-N-(1'-methyl-2'-methoxyethyl)-chloroacetanilide, can be used as herbicides.

These compounds are mainly active against millet-like grasses, for example Digitaria, Echinochloa, Panicum and Setaria. However, other important harmful grasses for example *Alopecurus myosuroides* and *Avena fatua* are affected by the above active compounds only if they are applied at high dosages. However, significant damage occurs to crop plants, for example sugar beet, soya beans or maize, when these relatively high dosages are used, so that the active compounds cannot be employed selectively in these crops.

The present invention now provides, as new compounds, the N-substituted halogenoacetanilides of the general formula

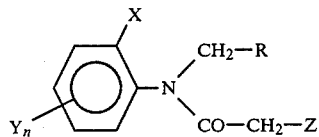

in which
R represents an optionally substituted N-containing heterocyclic radical,
X and Y, which may be identical or different, each represent alkyl,
Z represents halogen and
n represents 0, 1 or 2, Surprisingly, the N-substituted halogenoacetanilides according to the invention exhibit a considerably better herbicidal activity against important harmful grasses, such as *Alopecurus myosuroides* and *Avena fatua*, than the chloroacetanilides 2,6-diethyl-N-methoxymethyl-chloroacetanilide and 2-ethyl-6-methyl-N-(1'-methyl-2'-methoxymethyl)-chloroacetanilide, which are known from the state of the art and which are the most closely related substances chemically and from the point of view of their action. In contrast to the chloroacetanilides mentioned, it is possible to combat *Avena fatua* and/or Alopecurus at the same time as other harmful grasses, such as, for example, Digitaria, Echinochloa, Panicum or Setaria, in crops, such as beet, soya beans, beans, cotton, rapeseed, groundnuts, vegetables and maize, using the active compounds according to the invention. The active compounds according to the invention thus represent a substantial enrichment of the herbicidal agents to be used against grasses in the above crops.

In the formula supra R preferably represents a pyrazol-1-yl, imidazol-1-yl, 1,2,4-triazol-1-yl, 1,2,3-triazol-1-yl, 1,3,4-triazol-1-yl, 1,2,3,4-tetrazol-1-yl or pyrrol-1-yl radical that is optionally substituted by halogen (especially fluorine, chlorine or bromine) and/or alkyl with 1 to 4 carbon atoms, X and Y, which may be identical or different, each represent straight-chain or branched alkyl with 1 to 4 carbon atoms, and Z represents chlorine or bromine.

The invention also provides a process for the preparation of an N-substituted halogenoacetanilide of the formula (I) or an acid addition salt or metal salt complex thereof, in which an N-halogenomethyl-halogenoacetanilide of the general formula

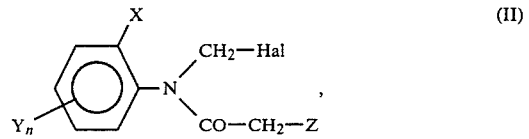

in which
X, Y, Z and n have the meanings stated above and
Hal represents halogen, especially chlorine or bromine,
is reacted with a heterocyclic compound of the general formula

in which
R has the meaning stated above and
M represents hydrogen or an alkali metal (especially sodium or potassium),
optionally in the presence of a diluent and an acid-binding agent. If desired the acid addition or metal is formed in the usual manner.

If 2,6-diethyl-N-chloromethyl-chloroacetanilide and pyrazole are used as starting materials, the course of the reaction can be represented by the following equation:

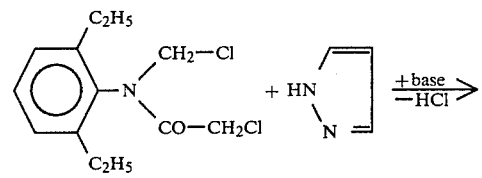

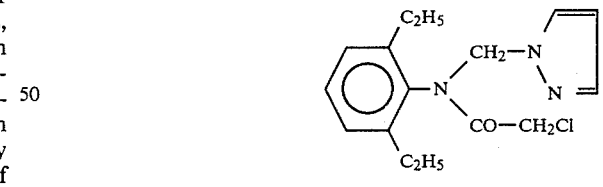

Examples which may be mentioned of the starting materials of the formula (II) are: 2-methyl-N-chloromethyl-chloroacetanilide, 2-methyl-N-bromomethyl-bromoacetanilide, 2-ethyl-N-bromomethyl-bromoacetanilide, 2-ethyl-N-chloromethyl-chloroacetanilide, 2-propyl-N-chloromethyl-chloroacetanilide, 2-isopropyl-N-chloromethyl-chloroacetanilide, 2-butyl-N-chloromethyl-chloroacetanilide, 2-isobutyl-N-chloromethyl-chloroacetanilide, 2-sec.-butyl-N-chloromethyl-chloroacetanilide, 2-tert.-butyl-N-chloromethyl-chloroacetanilide, 2,6-dimethyl-N-chloromethyl-chloroaceanilide, 2,6-diethyl-N-chloromethyl-chloroacetanilide, 2,6-diethyl-N-bromomethylbromoacetanilide, chloroacetanilide, 2-ethyl-6-methyl-N-chloromethyl-chloroacetanilide, 2,6-diisopropyl-N-chloromethyl-chloroacetanilide, 2,6-di-sec.-butyl-N-chloromethyl-chloroacetanilide, 2,3-dimethyl-N-chloromethyl-chloroacetanilide, 2,4-dimethyl-N-chloromethyl-chloroacetanilide, 2,5-dimethyl-N-chloromethyl-chloroacetanilide, 2-ethyl-3-methyl-N-chloromethyl-chloroacetanilide, 2-ethyl-4-methyl-N-chloromethyl-chloroacetanilide, 2-ethyl-5-methyl-N-chloromethyl-chloroacetanilide, 2,4,6-trimethyl-N-chloromethyl-chloroacetanilide, 2,4,5-trimethyl-N-chloromethyl-chloroacetanilide, 2,3,5-trimethyl-N-chloromethyl-chloroacetanilide, 2-ethyl-4,6-dimethyl-N-chloromethyl-chloroacetanilide, 2,6-diethyl-4-methyl-N-chloromethyl-chloroacetanilide and 2,6-diisopropyl-4-methyl-N-chloromethyl-chloroacetanilide.

The N-halogenomethyl-halogenoacetanilides of the formula (II) are known or can be prepared by known methods as illustrated in U.S. Pat. No. 3,630,716 and U.S. Pat. No. 3,637,847. They are obtained, for example, by reacting corresponding anilines with paraformaldehyde in the presence of catalytic amounts of potassium hydroxide and adding a halogenoacetyl halide, for example chloroacetyl chloride, to the phenylazomethines formed.

The N-halogenomethyl-halogenoacetanilides of the formula (II) can also be obtained by a new process in which known halogenoacetanilides of the general formula

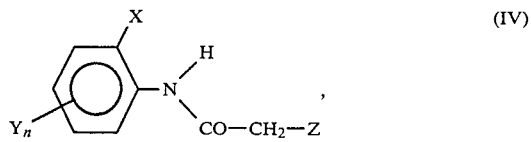

(IV)

in which X, Y, Z and n have the meanings stated above, are reacted with, per mole, at least 1 mole of formaldehyde (which may be supplied by substances which release formaldehyde, for example paraformaldehyde) and with a halogenating agent, such as hydrogen halide acid or an inorganic or organic acid halide, and a water-binding agent, for example sodium sulphate, in a manner which is in itself known at temperatures between $-10°$ C. and 150° C., preferably between 10° C. and 70° C., optionally in the presence of an inert organic solvent, for example toluene (see German Offenlegungsschriften Nos. 2,119,518 and 2,210,603. If inorganic acid halides, such as, for example, thionyl chloride, are used, one can dispense with the use of a specific water-binding agent. See the preparative Examples given later in this text.

The heterocyclic compounds of the formula (III) are compounds of organic chemistry which are known generally.

Preferred diluents for the reaction according to the present invention are inert organic solvents, especially ketones, such as diethyl ketone and, in particular methyl isobutyl ketone; nitriles, such as propionitrile and, in particular, acetonitrile; ethers, such as tetrahydrofuran or dioxan; aliphatic and aromatic hydrocarbons, such as petroleum ether, benzene, toluene or xylene, and halogenated hydrocarbons, such as methylene chloride, carbon tetrachloride, chloroform or chlorobenzene; esters, such as ethyl acetate; and formamides, such as, in particular, dimethylformamide.

Acid-binding agents which can be employed are any of the inorganic and organic acid acceptors which can be customarily used, especially alkali metal carbonates, for example sodium carbonate, potassium carbonate and sodium bicarbonate, and lower tertiary alkylamines, aralkylamines, aromatic amines or cycloalkylamines, such as, for example, triethylamine, dimethylbenzylamine, pyridine and diazabicyclooctane. It is also possible to use an appropriate excess of a compound of the formula (III).

The reaction temperatures in the process according to the invention can be varied within a relatively wide range. In general, the reaction is carried out at from 0° C. to 120° C., preferably from 20° C. to 80° C.

In carrying out the process according to the invention, 1 to 2 moles of the heterocyclic compound of the formula (III) and 1 mole of the acid-binding agent are preferably employed per mole of the compound of the formula (II). In order to isolate the compound of the formula (I), the reaction mixture is filtered and the filtrate is washed with water, dried and concentrated. The residue is optionally purified by fractional crystallisation or distillation.

In a particular form of working up, the reaction mixture is cooled to about 0° C. and filtered and hydrogen chloride is passed into the filtrate at 5° C. to $-15°$ C. The chloride salts which precipitate are filtered off, washed with an organic solvent, for example ethyl acetate, and partitioned in a mixture of an organic solvent, for example ethyl acetate, and water having a pH value of about 12. The organic phase is separated off and the compound of the formula (I) is isolated in the customary manner.

Acid addition salts of the compounds of the formula (I) can be prepared with all the physiologically acceptable acids. Preferred acids include hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtering, and can be optionally purified by washing with an inert organic solvent.

Metal salt complexes of the compounds of the formula (I) are preferably prepared using salts of metals of the main groups II to IV and of the sub-groups I and II and IV to VIII of the Periodic Table, amongst which copper, zinc, manganese, magnesium, tin, iron and nickel may be mentioned as examples. Possible anions of the salts are those which are derived from physiologically acceptable acids, preferably hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, for example by dissolving the metal salt in alcohol, for example ethanol, and adding the solution to the compound of the formula (I). Metal salt complexes can be isolated in a known manner, for example by filtering, and optionally be purified by re-crystallisation.

Examples which may be mentioned of particularly active compounds according to the invention are: 2,6-diethyl-N-(imidazol-1-yl-methyl)-chloroacetanilide, 2,6-diethyl-N-(1,3,4-triazol-1-yl-methyl)-chloroacetanilide, 2,6-diethyl-N-(pyrrol-1-yl-methyl)-chloroacetanilide, 2,6-dimethyl-N-(pyrazol-1-yl-methyl)-chloroacetanilide, 2,6-dimethyl-N-(imidazol-1-yl-methyl)-chloroacetanilide, 2,6-dimethyl-N-(1,2,4-triazol-1-yl-methyl)-chloroacetanilide, 2,6-dimethyl-N-(1,3,4-triazol-1-yl-methyl)-chloroacetanilide, 2,6-dimethyl-N-(pyrrol-1-yl-methyl)-chloroacetanilide, 2-ethyl-6-methyl-N-(imidazol-1-yl-methyl)-chloroacetanilide, 2-ethyl-6-methyl-N-(1,3,4-triazol-1-yl-methyl)-chloroacetanilide, 2-ethyl-6-methyl-N-(pyrrol-1-yl-methyl)-chloroacetanilide, 2-ethyl-4,6-dimethyl-N-(1,2,4-triazol-1-yl-methyl)chloroacetanilide, 2-ethyl-4,6-dimethyl-N-(1,3,4-triazol-1-yl-methyl)-chloroacetanilide, 2,4,6-trimethyl-n-(1,2,4-triazol-1-yl-methyl)-chloroacetanilide, 2,4,6-trimethyl-N-(1,3,4-triazol-1-yl-methyl)-chloroacetanilide, 2,6-diethyl-4-methyl-N-(1,2,4-triazol-1-yl-methyl)-chloroacetanilide, 2,6-diethyl-4-methyl-N-(1,3,4-triazol-1-yl-methyl)-chloroacetanilide, 2-isopropyl-N-(pyrazol-1-yl-methyl)-chloroacetanilide, 2-isopropyl-N-(1,2,4-triazol-1-yl-methyl)-chloroacetanilide, 2-isopropyl-N-(1,3,4-triazol-1-yl-methyl)-chloroacetanilide, 2-ethyl-N-(pyrazol-1-yl-methyl)-chloroacetanilide, 2-ethyl-N-(1,2,4-triazol-1-yl-methyl)-chloroacetanilide, 2-ethyl-N-(1,3,4-triazol-1-yl-methyl)-chloroacetanilide, 2,3-dimethyl-N-(pyrazol-1-yl-methyl)-chloroacetanilide, 2,3-dimethyl-N-(1,2,4-triazol-1-yl-methyl)-chloroacetanilide, 2,3-dimethyl-N-(1,3,4-triazol-1-yl-methyl)-chloroacetanilide, 2,4-dimethyl-N-(pyrazol-1-yl-methyl)-chloroacetanilide, 2,4-dimethyl-N-(1,2,4-triazol-1-yl-methyl)-chloroacetanilide, 2,4-dimethyl-N-(1,3,4-triazol-1-yl-methyl)-chloroacetanilide, 2,5-dimethyl-N-(pyrazol-1-yl-methyl)-chloroacetanilide, 2,5-dimethyl-N-(1,2,4-triazol-1-yl-methyl)-chloroacetanilide, 2,5-dimethyl-N-(1,3,4-triazol-1-yl-methyl)-chloroacetanilide, 2-methyl-N-(pyrazol-1-yl-methyl)-chloroacetanilide, 2-methyl-N-(1,2,4-triazol-1-yl-methyl)-chloroacetanilide, 2-methyl-N-(1,3,4-triazol-1-yl-methyl)-chloroacetanilide, 2-sec.-butyl-N-(pyrazol-1-yl-methyl)-chloroacetanilide, 2-sec.-butyl-N-(1,2,4-triazol-1-yl)-chloroacetanilide and 2-sec.-butyl-N-(1,3,4-triazol-1-yl)-chloroacetanilide. Other compounds are mentioned in the preparative Examples.

The active compounds according to the invention exhibit powerful herbicidal effects, especially against grasses. They can therefore be employed for the selective combating of weeds and especially of wild grasses. Crops in which they can be used are, in particular, beet, soya beans, beans, cotton, rapeseed, groundnuts, vegetables and maize.

The active compounds according to the invention can be applied either after or, in particular, before the emergence of the plants. They can also be worked into the soil before sowing.

The active compounds according to the invention influence plant growth and can therefore be used as defoliants, desiccants, agents for destroying broad-leaved plants, germination inhibitors and, especially, as weedkillers. By "weeds" in the broadest sense there are meant plants growing in places where they are not desired. Whether the compounds according to the invention act as total herbicides or selective herbicides depends essentially on the amount used.

The active compounds according to the present invention may be used, for example, to combat the following plants:

dicotyledon weeds such as mustard (Sinapis), cress (Lepidium), bed straw (Galium), chickweed (Stellaria), camomile (Matricaria), mayweed (Anthemis), gallant soldier (Galinsoga), goosefoot (Chenopodium), annual nettle (Urtica), groundsel (Senecio), pigweed (Amaranthus), purslane (Portulaca), cocklebur (Xanthium), bindweed (Convolvulus), morning glory (Ipomoea), knotweed (Polygonum), sesbania (Sesbania), ragweed (Ambrosia), spear thistle (Cirsium), common thistle (Carduus), sow thistle (Sonchus), field cress (Rorippa), toothcup (Rotala), false pimpernel (Linderna), deadnettle (Lamium), speedwell (Veronica), mallow (Abutilon), emex (Emex), thornapple (Datura), violet (Viola), hemp-nettle (Galeopsis), poppy (Papaver) and knapweed (Centaurea) and nightshade (Solanum); and monocotyledon weeds such as barnyard grass (Echinochloa), foxtail (Setaria), wild millet (Panicum), crabgrass (Digitaria), timothy (Phleum), bluegrass (Poa), fescue (Festuca), goosegrass (Eleusine), signalgrass (Brachiaria), ryegrass (Lolium), cheat (Bromus), oats (Avena), flatsedge (Cyperus), sorghum (Sorghum), quackgrass (Agropyron), Bermuda grass (Cynodon), Monocharia, fimbristylis (Fimbristylis), arrowhead (Sagittaria), spikerush (Eleocharis), bulrush (Scirpus), paspalum (Paspalum), Ischaemum, gooseweed (Sphenoclea), crowfoot grass (Dactyloctenium), redtop (Agrostis), meadow foxtail (Alopecurus) and silky bent-grass (Apera).

The active compounds according to the present invention may be used, for example, as selective herbicides in the following cultures:

dicotyledon cultures such as cotton (Gossypium), soya bean (Glycine), beet (Beta), carrot (Daucus), bean (Phaseolus), pea (Pisum), potato (Solanum), flax (Linum), sweet potato (Ipomoea), broad bean (Vicia), tobacco (Nicotiana), tomato (Lycopersicon), groundnut (Arachis), cabbage (Brassica), lettuce (Lactuca), cucumber (Cucumis) and marrow (Cucurbita); and monocotyledon cultures such as rice (Oryza), maize (Zea), wheat (Triticum), barley (Hordeum), oats (Avena), rye (Secale), sorghum (Sorghum), millet (Panicum), sugar cane (Saccharum), pineapple (Ananas), asparagus (Asparagus) and onion (Allium).

However, the use of the active compounds according to the invention is in no way restricted to these plants or even to the indicated genera but also embraces other plants, in the same way.

Depending on the concentration, the compounds can be used for the total combating of weeds, for example on industrial terrain and railway tracks and on paths and squares with and without trees. Equally, the compounds can be employed for combating weeds in perennial cultures, for example forestry plantings, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The active compounds according to the instant invention can be utilized, if desired, in the form of the usual formulation or compositions with conventional inert (i.e. plant compatible) diluents or extenders, i.e. diluents, carriers or extenders of the type usable in conventional pesticide formulations or compositions, e.g. conventional pesticide dispersible carrier vehicles such as gases, solutions, emulsion, wettable powders, suspensions, powder dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons (dichlorodifluoromethane or trichlorofluoromethane) as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.), as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially other plant protection agents, such as other insecticides, acaricides, fungicides, bactericides, rodenticides and fertilizers, if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The amount of active compound used can vary within a fairly wide range. It depends essentially on the nature of the desired effect. In general, the amounts used are from 0.1 to 20 kg of active compound per hectare, preferably from 0.2 to 15 kg/ha.

The active compounds according to the invention, as such or in their formulations, can be combined with other herbicidal active compounds to boost and supplement their spectrum of action, depending on the intended use; for this purpose, finished formulations or tank mixing may be employed.

The combinations of the active compounds according to the invention with 4-amino-3-methyl-6-phenyl-1,2,4-triazin-5(4H)-one (Metamitron) for beet cultures, 4-amino-6-tert.-butyl-3-methylthio-1,2,4-triazin-5(4H)-one (Metribuzin) for maize, soya beans, tomatoes and potatoes and 2-chloro-4-ethylamino-6-isopropylamino-1,3,4-triazine (Atrazin) for maize and sorghum should be singled out particularly.

The present invention also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The activity of the compounds of this invention is illustrated by the following biotest Examples.

In these Examples, the compounds according to the present invention are each identified by the number (given in brackets) of the corresponding preparative Example, which will be found later in this specification.

The known comparison compounds are identified as follows:

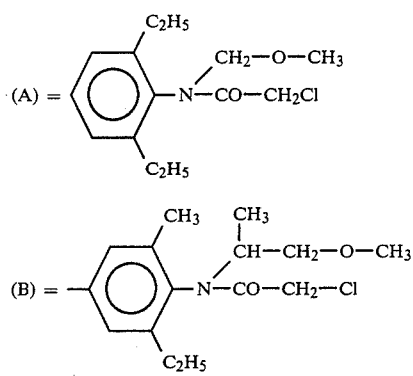

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:

0% = no action (like untreated control),
100% = total destruction.

The active compounds, the amounts applied and the results can be seen from the table which follows:

TABLE A

| | Greenhouse test, pre-emergence | | | | | |
|---|---|---|---|---|---|---|
| Active compound | Amount used, kg/ha | Sugar beet | Soya | Maize | Avena fatua | Echinochloa crusgalli | Alopecurus myosuroides |
| (A) | 0.625 | 0 | 0 | 0 | 75 | 90 | 60 |
| (B) | 0.625 | 0 | 0 | 0 | 65 | 90 | 40 |
| (1) | 0.625 | 0 | 0 | 0 | 100 | 100 | 100 |
| (2) | 0.625 | 0 | 0 | 0 | 95 | 95 | 100 |
| (5) | 0.625 | 0 | 0 | 0 | 100 | 100 | 100 |

PREPARATIVE EXAMPLES

EXAMPLE 1

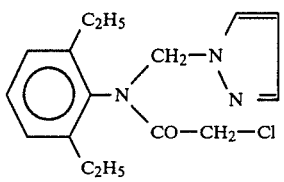

(1A)

A mixture of 68 g (1 mol) of pyrazole and 106 g (1.05 mol) of triethylamine in 150 ml of anhydrous ethyl acetate were added to 274.2 g (1 mol) of 2,6-diethyl-N-chloromethylchloroacetanilide in 250 ml of anhydrous ethyl acetate, whilst stirring, whereupon the temperature rose to 30° C. The mixture was stirred for a further 1 hour at room temperature. There were two possibilities for the working up:

(1) The reaction mixture was filtered and the filtrate was washed with water until neutral, dried over sodium sulphate and evaporated in vacuo. After fractional crystallisation with ligroin, 171.2 g (56% of theory) of 2,6-diethyl-N-(pyrazol-1-yl-methyl)-chloroacetanilide of melting point 67° C. were obtained in the form of colourless crystals.

(2) The reaction mixture was cooled to 0° C. and filtered and the residue on the filter was rinsed with 10 ml of cold ethyl acetate. 50 g (1.4 mol) of dry hydrogen chloride were passed into the filtrate at 0° to −10° C. The hydrochloride salt which had precipitated was then filtered off and rinsed with 50 ml of cold ethyl acetate and the solid residue was partitioned between 0.5 liter of ethyl acetate and 0.5 liter of an aqueous sodium hydroxide solution with a pH value of 12. The organic phase was separated off, washed twice with 0.5 liter of sodium chloride solution each time, dried over sodium sulphate and evaporated in vacuo. 60 ml of benzine were added to the colourless oily residue, whereupon the residue crystallised. 220.2 g (72% of theory) of 2,6-diethyl-N-(pyrazol-1-yl-methyl)-chloroacetanilide of melting point 67° C. were obtained in the form of colourless crystals.

The compounds listed in the table which follows were prepared in analogous manner:

TABLE 1

(I)

| Example No. | X | $Y_n$ | Z | R | Melting point (°C.) |
|---|---|---|---|---|---|
| 2 | $C_2H_5$ | 6-$C_2H_5$ | Cl | 1,2,4-Triazol-1-yl | 112 |
| 3 | i-$C_3H_7$ | 6-i-$C_3H_7$ | Cl | Pyrazol-1-yl | 134 |
| 4 | $CH_3$ | 6-$C_2H_5$ | Cl | 1,2,4-Triazol-1-yl | 92 |
| 5 | $CH_3$ | 6-$C_2H_5$ | Cl | Pyrazol-1-yl | 57 |
| 6 | $C_2H_5$ | 4,6-$(CH_3)_2$ | Cl | Pyrazol-1-yl | 82 |
| 7 | $CH_3$ | 4,6-$(CH_3)_2$ | Cl | Pyrazol-1-yl | 92 |
| 8 | $C_2H_5$ | 4-$CH_3$, 6-$C_2H_5$ | Cl | Pyrazol-1-yl | 78 |
| 9 | i-$C_3H_7$ | 6-i-$C_3H_7$ | Cl | 1,3,4-Triazol-1-yl | 196 |
| 10 | i-$C_3H_7$ | 6-i-$C_3H_7$ | Cl | 1,2,4-Triazol-1-yl | 138 |
| 11 | $C_2H_5$ | 6-$C_2H_5$ | Cl | Pyrrol-1-yl | Oil |
| 12 | i-$C_3H_7$ | — | Cl | 1,2,4-Triazol-1-yl | 118 |

TABLE 1-continued $$\text{(I)}$$

Structure: phenyl with X (ortho), Y_n, N substituted with CH₂—R and CO—CH₂—Z

| Example No. | X | Y_n | Z | R | Melting point (°C.) |
|---|---|---|---|---|---|
| 13 | CH₃ | 6-C₂H₅ | Cl | 1,2,3,4-Tetrazol-1-yl | Oil |
| 14 | i-C₃H₇ | — | Cl | Pyrazol-1-yl | Oil |
| 15 | C₂H₅ | — | Cl | 1,2,4-Triazol-1-yl | 81 |
| 16 | CH₃ | 6-CH₃ | Cl | Pyrazol-1-yl | 82 |
| 17 | CH₃ | 6-CH₃ | Cl | 1,2,4-Triazol-1-yl | 110 |
| 18 | CH₃ | 5-CH₃ | Cl | 1,2,4-Triazol-1-yl | Oil |
| 19 | CH₃ | — | Cl | Pyrazol-1-yl | 56 |
| 20 | CH₃ | — | Cl | 1,2,4-Triazol-1-yl | 88 |
| 21 | CH₃ | 5-CH₃ | Cl | Pyrazol-1-yl | Oil |
| 22 | CH₃ | 3-CH₃ | Cl | 1,2,4-Triazol-1-yl | 114 |
| 23 | CH₃ | 3-CH₃ | Cl | Pyrazol-1-yl | 102 |
| 24 | C₂H₅ | 6-CH₃ | Cl | Pyrazol-1-yl(× HCl) | 87 |
| 25 | C₂H₅ | 6-C₂H₅ | Cl | Pyrazol-1-yl(× HCl) | 67 |
| 26 | C₂H₅ | 6-C₂H₅ | Cl | 3,5-Dimethyl-pyrazol-1-yl | 111 |
| 27 | C₂H₅ | 6-C₂H₅ | Cl | Brom-methyl-pyrazolyl | 145 |
| 28 | C₂H₅ | 6-C₂H₅ | Cl | 3-Chlor-1,2,4-triazol-1-yl | 110 |
| 29 | CH₃ | 6-C₂H₅ | Cl | 3,5-Dimethyl-pyrazol-1-yl | 90 |
| 30 | C₂H₅ | 6-C₂H₅ | Cl | 3-Methyl-pyrazol-1-yl | 89 |
| 31 | C₂H₅ | 6-CH₃ | Cl | 3-Methyl-pyrazol-1-yl | 113 |
| 32 | C(CH₃)₃ | — | Cl | Pyrazol-1-yl | Oil |
| 33 | C(CH₃)₃ | — | Cl | 1,2,4-Triazol-1-yl | 118 |
| 34 | C₂H₅ | 6-CH₃ | Cl | Brom-methyl-pyrazolyl | 80 |
| 35 | CH₃ | 6-C₂H₅ | Cl | 4-Chlor-pyrazol-1-yl | 91 |
| 36 | CH₃ | 6-C₂H₅ | Cl | 3-Chlor-1,2,4-triazol-1-yl | 121 |
| 37 | C₂H₅ | 6-CH₃ | Cl | 2,4,5-Trichlor-imidazol-1-yl | 158 |
| 38 | C₂H₅ | 6-C₂H₅ | Cl | 4-Chlor-pyrazol-1-yl | 110 |
| 39 | C₂H₅ | 6-C₂H₅ | Cl | 1,2,3,4-Tetrazol-1-yl | 110 |
| 40 | C₂H₅ | 6-C₂H₅ | Br | Pyrazol-1-yl | 68 |
| 41 | CH₃ | 6-C₂H₅ | Br | Pyrazol-1-yl | 67 |
| 42 | C₂H₅ | 6-C₂H₅ | Cl | Imidazol-1-yl | Oil |
| 43 | C₂H₅ | 6-C₂H₅ | Br | 1,2,4-Triazol-1-yl | 90 |
| 44 | CH₃ | 6-C₂H₅ | Br | 1,2,4-Triazol-1-yl | 78 |

PREPARATION OF THE STARTING MATERIALS

EXAMPLE 1a

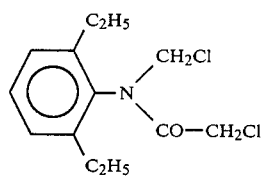

(Variant a)

45 g (1.5 mol) of paraformaldehyde were added to a solution of 225.7 g (1 mol) of 2,6-diethyl-chloroacetanilide in 1.5 liter of toluene. The mixture was warmed to 40° C. and 179 g (1.5 mol) of thionyl chloride were added dropwise, whilst stirring, whereupon vigorous evolution of gas started. Stirring was continued at 40° C. until the evolution of gas had ended. Thereafter, the mixture was filtered and the filtrate was concentrated in vacuo. After degassing the residue under a high vacuum, 268.7 g (98% of theory) of 2,6-diethyl-N-chloromethyl-chloroacetanilide were obtained as a colourless oil.

(Variant b)

45 g (1.5 mol) of paraformaldehyde and 100 g of anhydrous sodium sulphate were added to a solution of 225.7 g (1 mol) of 2,6-diethyl-chloroacetanilide in 1.5 liter of anhydrous toluene. Dry hydrogen chloride was passed in, whilst stirring and warming to 50° C., until the milky suspension of the paraformaldehyde had disappeared. Thereafter, a further 100 g of anhydrous sodium sulphate were added and the mixture was stirred for a further hour at 50° C. and filtered. The filtrate was concentrated in vacuo. After degassing the residue, 263.2 g (96% of theory) of 2,6-diethyl-chloroacetanilide were obtained as a colourless oil.

The compounds in Table 2 which follows were obtained analogously to Example 1a.

TABLE 2

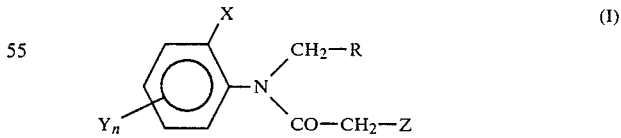

| Example No. | X | Y_n | Z | Hal | Melting point (°C.) |
|---|---|---|---|---|---|
| 3a | i-C₃H₇ | 6-i-C₃H₇ | Cl | Cl | — |
| 4a | CH₃ | 6-C₂H₅ | Cl | Cl | 91 |
| 6a | C₂H₅ | 4,6-(CH₃)₂ | Cl | Cl | — |
| 7a | CH₃ | 4,6-(CH₃)₂ | Cl | Cl | — |
| 8a | C₂H₅ | 4-CH₃ 6-C₂H₅ | Cl | Cl | — |
| 12a | i-C₃H₇ | — | Cl | Cl | 90 |
| 15a | C₂H₅ | — | Cl | Cl | — |
| 16a | CH₃ | 6-CH₃ | Cl | Cl | 88 |
| 18a | CH₃ | 5-CH₃ | Cl | Cl | — |
| 22a | CH₃ | 3-CH₃ | Cl | Cl | 40 |
| 32a | C(CH₃)₃ | — | Cl | Cl | — |
| 40a | C₂H₅ | 6-C₂H₅ | Br | Br | — |
| 41a | CH₃ | 6-C₂H₅ | Br | Br | — |

In the case of those Examples, where no melting point is mentioned in the above table, the compounds were not isolated.

What we claim is:

1. An N-substituted halogenoacetanilide of the formula $$\text{(I)}$$

in which
  R represents pyrazol-1-yl or substituted pyrazol-1-yl wherein the substituent is at least one of halogen and alkyl of 1 to 4 carbon atoms,
  X and Y which may be identical or different, each represent alkyl of 1 to 4 carbon atoms,
  Z represents chlorine or bromine and
  n represents 0, 1 or 2
and its acid addition salts.

2. A compound as claimed in claim 1 wherein R is pyrazol-1-yl.

3. A compound according to claim 1 having the formula

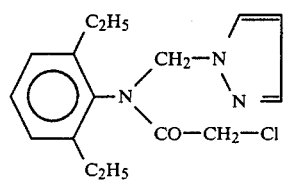

4. A compound according to claim 1 wherein R is a pyrazol-1-yl group, X is methyl, Y is ethyl at the 6th position and Z is chlorine.

5. A compound according to claim 1 wherein R is a pyrazol-1-yl group, X is ethyl, n is 2, Y is a methyl group at the 4th position and an ethyl group at the 6th position.

6. A compound according to claim 1 which is an acid addition salt of a physiologically acceptable acid.

7. An N-substituted halogenoacetanilide of the formula

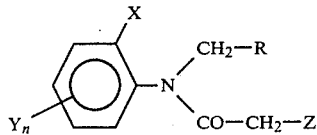

in which
R represents imidazol-1-yl or substituted imidazol-1-yl wherein the substitutent is at least one member of the group consisting of halogen and alkyl of 1 to 4 carbon atoms,
X and Y, which may be identical or different, each represent alkyl of 1 to 4 carbon atoms,
Z represents chlorine or bromine, and
n represents 0, 1 or 2
and its acid addition salts.

8. A herbicidal composition comprising a herbicidally effective amount of the compound of claim 1 in admixture with a solid or liquified gaseous diluent or carrier or in admixture with a liquid diluent or carrier containing a surface active agent.

9. A herbicidal composition as claimed in claim 8 wherein said compound is present in an amount of between 0.1 and 95% by weight.

10. A process of combating weeds which comprises applying to the weeds or to their habitat a compound according to claim 1 alone or in the form of a composition containing the same in a herbicidally effective amount in admixture with a diluent or carrier.

11. A process according to claim 10 wherein the active compound is applied to an area of agriculture in an amount of 0.1 to 10 kg per hectare.

12. A process according to claim 11 wherein the active compound is applied to an area of agriculture in an amount of 0.1 to 5 kg per hectare.

13. A process according to claim 10 wherein the said compound is applied before emergence of weeds.

14. A process according to claim 10 wherein said compound is applied to a field of sugar beet, soya or maize (corn).

15. A process according to claim 13 wherein said compound is applied to a field of sugar beet, soya or maize (corn).

16. A process according to claim 10 wherein said compound is applied to a field containing as a weed *Avena fatua, Echinochloa crusgalli* or *Alopecurus myosuroides*.

17. A process according to claim 13 wherein said compound is applied to a field containing as a weed *Avena fatua, Echinochloa crusgalli* or *Alopecurus myosuroides*.

* * * * *